United States Patent [19]

Fischer et al.

[11] Patent Number: 4,937,354
[45] Date of Patent: Jun. 26, 1990

[54] PREPARATION OF 3-(3,4,5,6-TETRAHYDRO-PHTHALIMIDO)-BENZALDEHYDES

[75] Inventors: Klaus Fischer; Lothar Rueb, both of Speyer; Peter Plath, Frankenthal, all of Fed. Rep. of Germany

[73] Assignee: BASF Aktiengesellschaft, Ludwigshafen, Fed. Rep. of Germany

[21] Appl. No.: 337,865

[22] Filed: Apr. 14, 1989

[30] Foreign Application Priority Data

May 4, 1988 [DE] Fed. Rep. of Germany ....... 3815042

[51] Int. Cl.$^5$ ............................................ C07D 209/48
[52] U.S. Cl. .................................. 548/513; 549/373; 549/451
[58] Field of Search ................ 548/476, 513; 549/373, 549/451

[56] References Cited

U.S. PATENT DOCUMENTS 4,551,264  11/1985  Eidenschink et al. ............... 549/373

FOREIGN PATENT DOCUMENTS 152465  1/1984  Japan .

OTHER PUBLICATIONS

Derwent Abstract of French Patent No. 2,479,824 (1981).
M. Tanaka, Bulletin of the Chemical Society of Japan, vol. 40, No. 7, pp. 1724–1726 (1967).
Derwent Publication 85-233795/38 [JP-A 60/152,465].

*Primary Examiner*—Mary E. Ceperley
*Attorney, Agent, or Firm*—Keil & Weinkauf

[57] ABSTRACT

3-(3,4,5,6-Tetrahydrophthalimido)-benzaldehydes of the type I

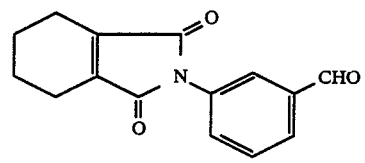

or corresponding derivatives substituted in the phenyl ring are prepared by (a) acetalization of a 3-nitrobenzaldehyde III or of a corresponding derivative with an alcohol IV in the presence of an acidic catalyst to give the corresponding cyclic acetal V

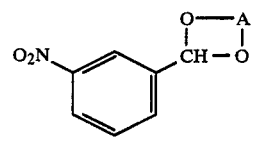

(b) reduction of the cyclic acetal V with hydrogen to give the corresponding amino compound II and
(c) subsequent condensation of this aminophenyl acetal II with 3,4,5,6-tetrahydrophthalic anhydride in an acidic reaction medium.

3 Claims, No Drawings

PREPARATION OF 3-(3,4,5,6-TETRAHYDRO-PHTHALIMIDO)-BENZALDEHYDES

The present invention relates to a novel process for the preparation of 3-(3,4,5,6-tetrahydrophthalimido)-benzaldehydes (I).

The present invention furthermore relates to novel 3-(3,4,5,6-tetrahydrophthalimido)-benzaldehydes of the general formula Ia

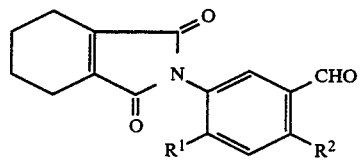

where $R^1$ is hydrogen or halogen and $R^2$ is halogen, with the proviso that $R^2$ is not chlorine when $R^1$ is fluorine, and novel intermediates of Ia of the general formula IIa

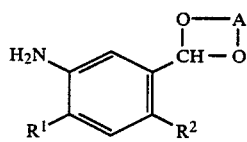

where A is a 1,2-ethylene or 1,3-propylene bridge, and these bridge members may in turn carry up to three $C_1$-$C_3$-alkyl groups.

JP-A 60/152 465 discloses that 3-nitrobenzaldehydes can be reduced with iron in an acetic acid medium to give the corresponding 3-aminobenzaldehydes and the latter can then be converted with 3,4,5,6-tetrahydrophthalic anhydride into the compounds of the type I:

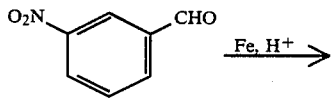

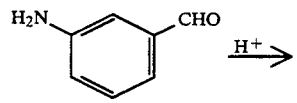

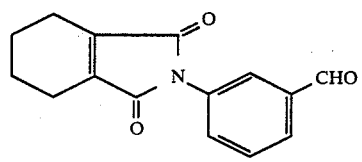

The disadvantages of this process are that the reduction with iron is involved in terms of process engineering and that the aminobenzaldehydes tend to undergo autocondensation, resulting in unsatisfactory yields of the products, which furthermore are obtained only in insufficient purity.

It is an object of the present invention to provide a universally applicable process for the preparation of 3-(3,4,5,6-tetrahydrophthalimido)-benzaldehydes of the type I, in particular the novel compounds Ia and their intermediates IIa.

We have found that this object is achieved by a novel process for the preparation of 3-(3,4,5,6-tetrahydrophthalimido)-benzaldehydes of the type I, wherein (a) the aldehyde group of a 3-nitrobenzaldehyde III is reacted with an alkanediol HO—A—OH IV, where A is a 1,2-ethylene or 1,3-propylene chain and this chain may in turn carry up to three $C_1$-$C_3$-alkyl groups, in an inert organic solvent in the presence of an acidic catalyst to give the corresponding cyclic acetal V, (b) the cyclic acetal V is reduced catalytically with hydrogen to give the corresponding amino compound II and (c) this aminophenyl acetal II is condensed with 3,4,5,6-tetrahydrophthalic anhydride in an acidic reaction medium, the water liberated during the cyclization effecting deacetalization of the formyl group, and the desired (3,4,5,6-tetrahydrophthalimido)-benzaldehyde I being formed directly.

The novel compounds Ia and IIa defined at the outset

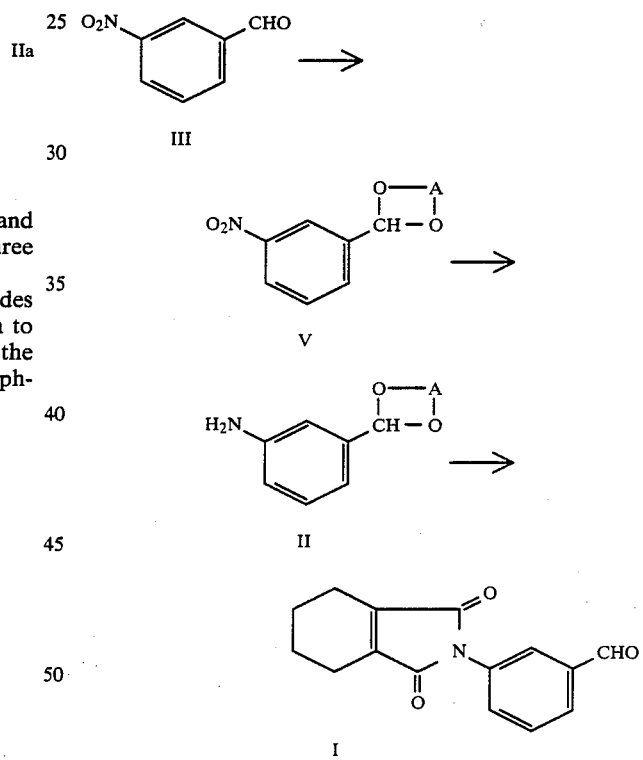

have also been found.

The conversion of the nitrophenylaldehyde III into the nitrophenyl acetal V takes place in a conventional manner [Houben-Weyl Vol. VI. 3, page 203 et seq.] in an inert organic solvent in the presence of an acidic catalyst at from 25° to 150° C., preferably from 80° to 120° C., the water formed during the reaction being removed continuously from the reaction mixture.

Examples of suitable acidic catalysts are inorganic acids, such as hydrochloric acid, sulfuric acid and phosphoric acid; organic carboxylic, sulfonic and phosphonic acids, in particular aliphatic and aromatic sulfonic acids (methanesulfonic acid, trifluoromethanesulfonic acid, benzenesulfonic acid and toluenesulfonic acid), and salts, such as iron(III) chloride, zinc(II) chloride and sodium bisulfate, the catalyst concentration being from 0.01 to 10, preferably from 0.1 to 1, mol %, based on the educt III. Preferred solvents are inert organic solvents which are capable of forming azeotropes with water, provided that the educts and/or products are partially or completely soluble therein. Examples of suitable solvents are aromatic hydrocarbons, such as benzene, toluene and xylene; aliphatic hydrocarbons, such as hexane, heptane and cyclohexane; chlorohydrocarbons, such as chloroform, carbon tetrachloride, 1,2-dichloroethane and chlorobenzene, and ethers, such as diethyl ether, methyl butyl ether and diisopropyl ether.

The nitrophenyl acetal V is isolated by a conventional method.

The acetal V thus obtained is then reduced with hydrogen over a metal or noble metal catalyst to give the aminoacetal II.

Suitable catalysts are platinum, palladium, rhodium, ruthenium and rhenium, Raney nickel being particularly advantageous. The catalyst concentration is advantageously from 10 to 30% by weight, based on the educt V. The reaction is carried out in an inert protic or aprotic polar organic solvent, such as an alcohol, such as methanol, ethanol, isopropanol or glycol, a carboxylic acid, such as acetic acid or propionic acid, or an ether, such as those mentioned above or tetrahydrofuran or dioxane, or mixtures of these, at from 0° to 100° C., preferably from 25° to 50° C., and under a hydrogen pressure of from 1 to 50, in particular 1 to 10, bar.

The aminophenyl acetal II is isolated from the reaction mixture in general in a conventional manner and then condensed with 3,4,5,6-tetrahydrophthalic anhydride by a conventional method.

The condensation is usually carried out in a protic polar solvent, such as acetic acid or propionic acid or a mixture of these, at from 50° to 150° C., preferably from 70° to 120° C. Under these reaction conditions, cleavage of the acetal group to form the aldehyde function takes place at the same time.

The nitrobenzaldehydes III required for the process are known from the literature or can be prepared by known processes (Houben-Weyl, Vol. E3).

Other suitable starting compounds for the novel process, in addition to 3-nitrobenzaldehyde as the parent substance, are derivatives which are substituted in the nucleus, provided that their substituents are inert under the reaction conditions. Examples of suitable substituents are halogen, in particular fluorine, chlorine and bromine, hydroxyl, alkyl, alkoxy, dialkylamino and alkoxycarbonyl; alkyl radicals in these groups are preferably of not more than 12 carbon atoms and in turn may carry halogen atoms, preferably fluorine or chlorine, hydroxyl or $C_1$-$C_4$-alkoxy.

Preferred compounds III, and hence preferred products I, are those which correspond to the novel compounds Ia and IIa, including in particular the substances stated in Tables A and B below.

TABLE A

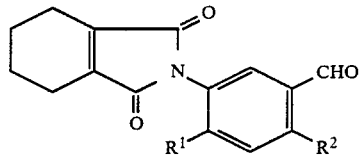

Ia

| $R^1$ | $R^2$ |
|---|---|
| H | F |
| H | Cl |
| H | Br |
| F | F |
| F | Br |
| Cl | F |
| Cl | Cl |
| Cl | Br |
| Br | F |
| Br | Cl |
| Br | Br |

TABLE B

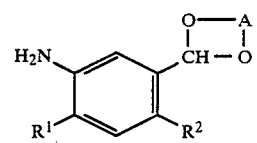

Ib

| $R^1$ | $R^2$ | A |
|---|---|---|
| H | F | —CH$_2$CH$_2$— |
| H | Cl | —CH$_2$CH$_2$— |
| H | Br | —CH$_2$CH$_2$— |
| F | F | —CH$_2$CH$_2$— |
| F | Br | —CH$_2$CH$_2$— |
| Cl | F | —CH$_2$CH$_2$— |
| Cl | Cl | —CH$_2$CH$_2$— |
| Cl | Br | —CH$_2$CH$_2$— |
| Br | F | —CH$_2$CH$_2$— |
| Br | Cl | —CH$_2$CH$_2$— |
| Br | Br | —CH$_2$CH$_2$— |
| H | F | —CH$_2$CH$_2$CH$_2$— |
| H | Cl | —CH$_2$CH$_2$CH$_2$— |
| H | Br | —CH$_2$CH$_2$CH$_2$— |
| F | F | —CH$_2$CH$_2$CH$_2$— |
| F | Br | —CH$_2$CH$_2$CH$_2$— |
| Cl | F | —CH$_2$CH$_2$CH$_2$— |
| Cl | Cl | —CH$_2$CH$_2$CH$_2$— |
| Cl | Br | —CH$_2$CH$_2$CH$_2$— |
| Br | F | —CH$_2$CH$_2$CH$_2$— |
| Br | Cl | —CH$_2$CH$_2$CH$_2$— |
| Br | Br | —CH$_2$CH$_2$CH$_2$— |

The 3-(3,4,5,6-tetrahydrophthalimido)-benzaldehydes I are useful intermediates for the preparation of herbicides and growth regulators of the general structure VI

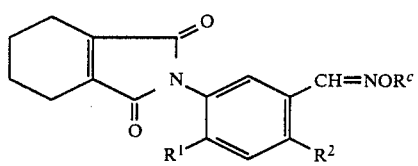

VI

Active ingredients of this type are described in, for example, DE-A 3 607 300 and JP 60/152 465.

The Examples which follow illustrate the novel process for the preparation of the compounds I:

EXAMPLE I

The experiments listed in Tables 1, 2 and 3 below were carried out similarly to this Example.

TABLE 1

Reaction of the nitrobenzaldehydes III with alkanediols IV to give the corresponding nitrophenyl acetals V in toluene in the presence of p-toluenesulfonic acid (acidic catalyst)

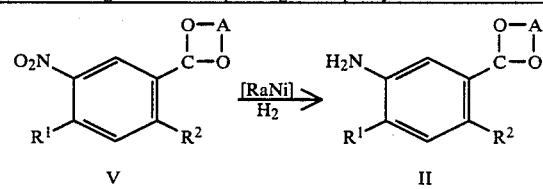

| Example No. | $R^1$ | $R^2$ | A | Mol III | Mol IV | mmol acidic cat. | ml toluene | T [°C.] | Yield V [%] |
|---|---|---|---|---|---|---|---|---|---|
| 2a | F | Cl | $-(CH_2)_3-$ | 0.10 | 0.11 | 0.10 | 250 | 85 | 92 |
| 3a | F | F | $-(CH_2)_3-$ | 0.05 | 0.055 | 0.05 | 200 | 85 | 90 |
| 4a | H | F | $-(CH_2)_2-$ | 0.05 | 0.055 | 0.05 | 200 | 85 | 98 |

TABLE 2

Reduction of the nitrophenyl acetals V with hydrogen in tetrahydrofuran (THF) with hydrogen in the presence of Raney nickel (RaNi) to give the corresponding aminophenyl acetals II

| Example No. | Compound V | Mol V | Mol $H_2$ | Pressure $H_2$ [bar] | RaNi [% by wt., based on V] | THF [ml] | T [°C.] | Yield II [%] |
|---|---|---|---|---|---|---|---|---|
| 2b | 2a | 0.05 | 0.15 | 1.05 | 23 | 150 | 40 | 78 |
| 3b | 3a | 0.05 | 0.15 | 1.05 | 24 | 150 | 40 | 98 |
| 4b | 4a | 0.05 | 0.15 | 1.05 | 28 | 150 | 45 | 87 |

Preparation of 2-chloro-5-(3,4,5,6-tetrahydrophthalimido)-benzaldehyde (a) A solution of 371 g (2.00 moles) of 2-chloro-5-nitrobenzaldehyde, 137 g (2.2 moles) of ethylene glycol, 1 g of p-toluenesulfonic acid and 1.5 l of toluene was stirred for 5 hours at the boiling point, the water of reaction being removed continuously. Thereafter, the solvent was removed under reduced pressure, the ethylene glycol acetal of the 2-chloro-5-nitrobenzaldehyde being obtained as a residue, in virtually quantitative yield. The melting point of a purified sample was 88°–90° C.

(b) 115 g (0.5 mole) of the ethylene glycol acetal of (a) in 1 l of tetrahydrofuran were hydrogenated in the presence of 20 g of Raney nickel under a hydrogen pressure of 1.05 bar at 50° C. After being worked up in a conventional manner, the reaction solution gave the ethylene glycol acetal of the 5-amino-2-chlorobenzaldehyde as an oil in virtually quantitative yield.

(c) A solution of 99.8 g (0.5 mole) of the 5-amino-2-chlorobenzaldehyde acetal from (b), 76.1 g (0.5 mole) of 3,4,5,6-tetrahydrophthalic anhydride and 0.5 l of glacial acetic acid was stirred for 5 hours at the boiling point. The reaction mixture thus obtained was cooled to 25° C. and 0.5 l of water was added, 2-chloro-5-(3,4,5,6-tetrahydrophthalimido)-benzaldehyde being precipitated. Yield: 83%; mp.: 140°–141° C.

TABLE 3

Condensation of the aminoacetals II with 3,4,5,6-tetrahydrophthalic anhydride (THPA) in glacial acetic acid (HAc) to give the corresponding 3-[3,4,5,6-tetrahydrophthalimido]-benzaldehydes I

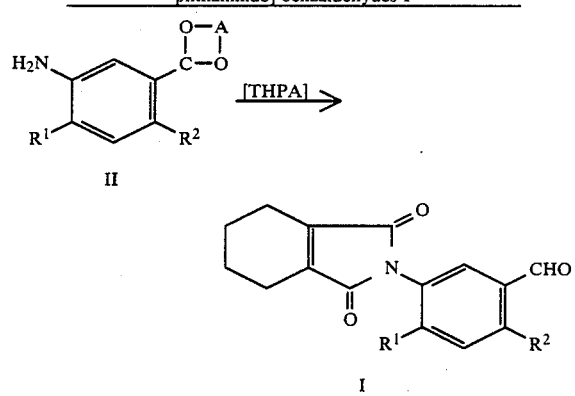

| Example No. | Compound II | Mol II | Mol THPA | ml HAc | T [°C.] | Yield I [%] |
|---|---|---|---|---|---|---|
| 2c | 2b | 0.02 | 0.02 | 100 | 70 | 16 |
| 3c | 3b | 0.01 | 0.01 | 50 | 70 | 69 |
| 4c | 4b | 0.01 | 0.01 | 50 | 70 | 73 |

We claim:

1. A process for the preparation of a 3-(3,4,5,6-tetrahydrophthalimido)-benzaldehyde of the type I

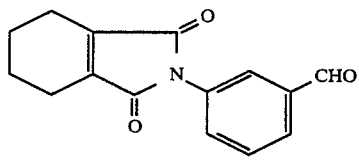   I or of a corresponding derivative substituted in the phenyl ring, wherein
(a) the formyl group of a 3-nitrobenzaldehyde III

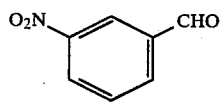   III or of a corresponding derivative substituted in the phenyl nucleus is condensed with an alcohol IV

HO—A—OH   IV where A is a 1,2-ethylene or 1,3-propylene chain and this chain may in turn carry up to three $C_1$–$C_3$-alkyl groups, in an inert organic solvent in the presence of an acidic catalyst to give the corresponding cyclic acetal V

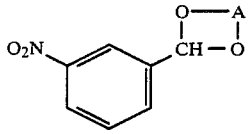   V (b) the cyclic acetal V is reduced catalytically with hydrogen to give the corresponding amino compound II

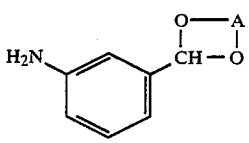   II and
(c) this aminophenyl acetal II is condensed with 3,4,5,6-tetrahydrophthalic anhydride in an acidic reaction medium and at the same time the acetal group is cleaved to give the aldehyde group again.

2. A process as claimed in claim 1, wherein p-toluenesulfonic acid is used as the catalyst in the acetalization of the nitroformylbenzene III.

3. A process as claimed in claim 1, wherein the condensation of the aminophenylacetal II with tetrahydrophthalic anhydride is carried out in the presence of a lower carboxylic acid.

* * * * *